United States Patent [19]
Das

[11] Patent Number: 5,554,181
[45] Date of Patent: Sep. 10, 1996

[54] STENT

[75] Inventor: Gladwin S. Das, St. Paul, Minn.

[73] Assignee: Regents of the University of Minnesota, Minneapolis, Minn.

[21] Appl. No.: 237,626

[22] Filed: May 4, 1994

[51] Int. Cl.⁶ .................................................... A61F 2/06
[52] U.S. Cl. .............................................. 623/1; 606/194
[58] Field of Search ......................... 623/1, 12; 606/191, 606/194, 198

[56] References Cited

U.S. PATENT DOCUMENTS

| | | |
|---|---|---|
| 4,140,126 | 2/1979 | Choudhury . |
| 4,795,458 | 1/1989 | Regan . |
| 4,820,298 | 4/1989 | Leveen et al. . |
| 4,830,003 | 5/1989 | Wolff et al. . |
| 4,856,516 | 8/1989 | Hillstead . |
| 4,886,062 | 12/1989 | Wiktor . |
| 4,969,458 | 11/1990 | Wiktor . |
| 4,990,155 | 2/1991 | Wilkoff . |
| 5,019,090 | 5/1991 | Pinchuk . |
| 5,026,377 | 6/1991 | Burton et al. . |
| 5,035,706 | 7/1991 | Giantureo et al. . |
| 5,037,427 | 8/1991 | Harada et al. . |
| 5,064,435 | 11/1991 | Porter . |
| 5,078,720 | 1/1992 | Burton et al. . |
| 5,104,404 | 4/1992 | Wolff . |
| 5,116,365 | 5/1992 | Hillstead . |
| 5,122,154 | 6/1992 | Rhodes ................................... 606/198 |
| 5,133,732 | 7/1992 | Wiktor . |
| 5,135,536 | 8/1992 | Hillstead ................................ 606/195 |
| 5,144,423 | 5/1992 | Kasprzyk et al. . |
| 5,147,370 | 9/1992 | McNamara et al. . |
| 5,161,547 | 11/1992 | Tower . |
| 5,186,167 | 2/1993 | Kolobow . |
| 5,190,058 | 3/1993 | Jones et al. . |
| 5,192,297 | 3/1993 | Hull . |
| 5,217,483 | 6/1993 | Tower . |
| 5,226,913 | 7/1993 | Pinchuk . |
| 5,354,309 | 10/1994 | Schnepp-Pesch et al. ............. 606/198 |
| 5,405,377 | 4/1995 | Cragg .......................................... 623/1 |

FOREIGN PATENT DOCUMENTS

| | | |
|---|---|---|
| 540290 | 5/1993 | European Pat. Off. ................... 623/1 |
| 0566245A1 | 3/1993 | United Kingdom . |
| WO91/12779 | 9/1991 | WIPO . |
| 92/009246 | 6/1992 | WIPO ...................................... 623/1 |
| WO92/11824 | 7/1992 | WIPO . |
| WO92/19310 | 11/1992 | WIPO . |

OTHER PUBLICATIONS

C. Dotter, et al., entitled "Technical Developments and Instrumentation".
H. Hyodo et al., *Clinical Radiology*, 34, 571–576 (1990).
M. Maeda, et al., *J. Vascular and Interventional Radiology*, 3(3), 565–569, (1992).
Tatsuo Nakamura, *J. Jpn. Bronchoesophagol. Soc.*, 43(2), 124–128, (1992).
V. K. Rauber, et al., *Fortschr. Rontgenstr.*, 153(2), 698–701 (1990).
L. M. Schetky, *Scientific American*, 241(5), 74–82, (1979).
H. Takakura et al., *Jpn. J. Artif. Organs.*, 19(3), 1275–1277 (1990).
R. Tominaga, et al. *Am. Heart J.*, 123, 21–28 (1992).
M. Williams, et al., *Progress in Cardiology*, 3(2), 79–94.
H. Yoshida, et al., *Asaio Transactions*, 37, M272–M273.
C. L. Zollikoffer, et al., *Cardiovasc. Intervent. Radiol.*, 15, 272–278, (1992).

(List continued on next page.)

*Primary Examiner*—Michael J. Milano
*Attorney, Agent, or Firm*—Merchant, Gould, Smith, Edell, Welter & Schmidt, P.A.

[57] ABSTRACT

A stent comprising a self-expandable cylindrical body constructed out a single integral piece of material, including a plurality of wavy closed windings and strips interconnecting the windings such that the stent is prevented from stretching longitudinally is provided. The stent is self-expandable from a first radially-constrained, unexpanded diameter to a second, radially-unconstrained, expanded diameter. The stent can be implanted within a body cavity of an animal to maintain patency thereof.

10 Claims, 6 Drawing Sheets

OTHER PUBLICATIONS

C. Dotter, et al., entitled "Technical Developments and Instrumentation—Transluminal Expandable Nitinol Coil Stent Grafting: Preliminary Report" *Radiology* 147, 259–266, Apr., 1983.

"Oesophageal Strictures, Treatment by Slow Continuous Dilation", by C. C. Didcott F.R.C.S., *Annals of the Royal College of Surgeons of England* 1973, vol. 53, pp. 112–126.

STENT

FIELD OF THE INVENTION

The present invention relates to a stent to be deployed inside a cavity of an animal for maintaining patency of the cavity. This invention also relates to a method of making and positioning such a stent in the body cavity of an animal.

BACKGROUND OF THE INVENTION

In many diseases, a body cavity, such as a passageway or channel (e.g. blood vessel, esophagus, bronchus, etc.) through which a body fluid or other substance (e.g., air in bronchus) flows, may collapse or be narrowed to be substantially restricted. A passageway can be so restricted that fluid flow in the passageway is diminished or blocked. For example, in coronary artery disease, the coronary artery of a mammal is narrowed or restricted such that blood flow through the artery is diminished. Even after balloon angioplasty procedures, such as percutaneous transluminal angioplasty, in which a blood vessel is dilated by means of a balloon catheter to flatten plaque against the artery wall, in many cases, restenosis occurs soon afterwards and the vessel becomes restricted again. Following percutaneous balloon angioplasty, the arterial wall sometimes develops tears. As a result, flaps of the inner layer of the arterial wall may hang loosely in the blood vessel, causing obstruction to blood flow and requiring emergency bypass surgery. There is a need for a means to maintain patency of collapsing body cavities or blood vessels and to prevent the renarrowing of the vessel after angioplasty.

Stents can be used to provide mechanical support to maintain the patency of blood vessels. Similarly, the patency of body cavities and passageways such as urethra, bile duct, esophagus, ureters, aorta, etc., can also be maintained by stents. Stents of various shapes and designs have been utilized for such purposes. For example, U.S. Pat. No. 4,886,062 (Wiktor) discloses an intravascular radially expandable stent and method of implantment thereof. The stent disclosed by Wiktor comprises a wire wound into a continuous helix along the length of the stent. The stent is made of a low-memory metal and is radially expanded by inflating a catheter balloon, which exerts a force on the stent. U.S. Pat. No. 4,969,458 (Wiktor) also discloses a stent made of low-memory metal, expandable radially to a larger diameter by the action of inflation of a balloon. U.S. Pat. No. 5,133,731 (Wiktor) discloses yet another stent made of low-memory material. The stent has a cylindrical body coiled from a generally continuous wire with a deformable zig-zag structure. Means for preventing the stent's body from stretching along its longitudinal axis are also present in the stent.

Because stents made with low-memory materials require mechanical force to expand the stent, such as a force exerted by the inflation of a balloon, their use can result in trauma to the body caused by the imprecise control of the expansion of the stent or the balloon. Moreover, stents made with low memory material may have a tendency to be compressed into a smaller diameter by the radial, inwardly directed force exerted by the body tissue on the stent. Self-expanding stents have been developed to obviate the use of externally applied mechanical force for their expansion. For example, U.S. Pat. No. 4,830,003 (Wolff) discloses a cylindrical stent for preventing arterial closure and restenosis. The stent is made of biocompatible metal wires welded together in pairs at alternate ends with each pair of wires bent into a V-section. The stent is compressed and loaded into an outer catheter, positioned in a selected location and released for self-expansion by an inner catheter. U.S. Pat. No. 5,104,404 (Wolff) discloses an articulated stent made up of a number of individual stent segments. A number of wires are welded together to form a segment, and adjacent stent segments are connected together to provide a hinge action. In a similar fashion, U.S. Pat. No. 5,035,706 (Gianturco) discloses a self-expanding stent formed of stainless steel wire arranged in a closed zig-zag configuration including an endless series of straight sections joined at their ends by bends. The bends of at least one end of the stent are formed into eyes for connection with eyes at one end of a similarly constructed stent. The stents are compressible into reduced diameter size for insertion into and removal from a body passageway.

Because self-expanding stents, such as those made from stainless steel, once expanded, cannot be deformed unless an external force is applied thereto, such stents generally cannot be removed from the body cavity once they are deployed therein. Therefore, stents that can be brought back to a smaller shape and size after expansion within a body cavity have been developed to enable removal after deployment. For example, U.S. Pat. No. 5,037,427 (Harada et al.) discloses a method of implanting a stent and removing same from a tubular organ. The stent is formed of a two-way shape-memory alloy and expands or shrinks in the radial direction, in accordance with changes in temperature. Also, U.S. Pat. No. 5,147,370 (McNamara et al.) discloses a coil stent constructed from a nitinol alloy. However, because such stents expand by the heat of the body, there can be a risk that such a stent would expand before it is properly deployed or positioned in the desired location.

U.S. Pat. No. 5,026,377 (Burton) discloses a stent placement instrument and method for deployment or retraction of a self-expanding stent in a body canal. The instrument comprises an elongated tubular outer sleeve having disposed therein an elongated core which is movable relative to the sleeve and has a grip member for releasably holding a self-expanding stent within the outer sleeve. U.S. Pat. No. 5,078,720 (Burton) discloses yet another stent placement instrument and method for the placement of a self-expanding stent in a body canal. The instrument comprises an elongated inner tube having an outer tube disposed along its axis for carrying and retaining a self-expanding stent and an arrangement for releasing the stent, in combination with at least one of: (a) a location member for positioning and fixing the instrument so that the stent is released at a desired location in the body canal, and (b) a member for releasing the stent in a retrograde manner. The stents disclosed by Burton in the two patents are wire-mesh-type stents.

SUMMARY OF THE INVENTION

The present invention provides a stent having an elongated (e.g., generally cylindrical) body which includes a plurality of generally closed windings (or loops) and strips interconnecting the windings such that the stent is prevented from stretching longitudinally (or along its axis). The cylindrical body is constructed from a single piece of material such as a wire. The stent is self-expandable from a first, radially-constrained, unexpanded geometry to a second, radially-unconstrained, expanded geometry. The strips can be interconnected to form an aligned, longitudinally oriented spine which helps to prevent longitudinal stretching of the stent, thus maintaining the geometry thereof. The windings can further have curves (or waves) which, for example, can have a generally sinusoidal appearance. The stent of present invention, being capable of self-expansion, is effective for supporting and maintaining patency of a body cavity, such as a passageway (e.g., artery, aorta, bile duct, urethra) through which a fluid flows. Such a stent can be implanted in a body cavity of an animal, such as a mammal, including humans.

In another aspect, the present invention provides a stent comprising a self-expandable cylindrical body formed from a continuous wire. The cylindrical body is a coil having successive windings of wire wherein each of the windings (or loops) is an essentially closed, complex loop. The term "complex loop" refers to a loop that has curves (or waves) or structures such as o-shaped eyelets on the loop. The stent is formed such that it is prevented from stretching longitudinally (or axially) by portions of wire interconnecting adjacent windings. When compressed and put under radial pressure by a radial constraint, such as a sheath of a catheter, which prevents the stent from expanding radially outward, the stent has a first diameter reflecting the dimensions of the constraint. When the radial constraint is removed, the stent can self-expand from the first radially-constrained, unexpanded diameter to a second, radially-unconstrained, expanded diameter. The stent can be wound such that any two adjacent windings (for example, a first and second successive windings), are connected and restrained from stretching longitudinally by a portion (or strip) of wire interposed between the first and second successive windings and intertwining with a portion of one of said two adjacent windings. The portion of the wire interposed between the two successive windings can be connected to a first end or end portion of the first winding and an end or end portion of the second winding and intertwined with a second end portion of the first winding to prevent stretching longitudinally. The intertwining of the wire interposed between successive windings can be aligned to result in a generally straight longitudinal spine (or cord) in the stent. The stent can be formed from a single, continuous wire into such a coil having successive windings.

The present invention also provides a method of making a stent. The method includes a step of winding a wire on a cylindrical mandrel to form a self-expanding coil of successive windings (or loops) such that each of the windings having curves and that the coil is prevented from stretching longitudinally by portions of the wire connecting the successive windings. Spikes can be used on the mandrel for the wire to be wound thereupon. The wire can be wound such that the portion of wire connecting any adjacent first and second successive windings is connected to a first end portion of the first winding and an end portion of the second winding and intertwined with a second end portion of the first winding.

The mandrel can be disassemblable (or capable of being taken apart) to enable a formed or wound stent to be removed therefrom without distortion. Such a disassemblable mandrel can contain a elongated, preferably generally cylindrical body with spikes disposed thereon for a wire to be wound to form the stent. The cylindrical body can contain disassemblable longitudinal layers. In another aspect, the spikes can be movably affixed on the cylindrical body, for example, by screwing into the cylindrical body.

The stent can be made with a flexible material, for example, a shape-memory material such as nitinol. In the preferred embodiment, the stent is made of "superelastic" nitinol, which is an alloy containing equal parts of nickel and titanium. A stent made with such a superelastic nitinol, upon annealing at an elevated temperature, gains memory of the shape in which it is annealed (i.e., a preprogrammed shape). If deformed into other shapes, upon release, the stent will spring back to its preprogrammed shape. The method of making the stent can include annealing the wound coil on the mandrel at an elevated temperature above room temperature, preferably at above 500° C., more preferably about 500° C., for a determined period, for example, about 30 minutes.

Also provided by the present invention is a system for positioning (or deploying) in a body cavity a self-expandable stent. This system includes an instrument for placement (or deployment) of a self-expanding stent and a self-expanding stent releasably held by the instrument. In this system, the stent includes a self-expandable, cylindrical body formed by a continuous wire. The cylindrical body is a coil of successive windings each having curves and the stent is prevented from stretching in its longitudinal axis. The stent is self-expandable from a first radially-constrained, unexpanded diameter to a second, radially-unconstrained, expanded diameter.

The instrument can include an elongated tubular outer sheath (or sleeve) having a first end and a second end, such as a conventional catheter, for radially constraining the stent proximate the distal end of the instrument, and an elongated core or pusher device having a first end and a second end movably disposed within the lumen of the sheath. As used herein, the term "proximal" means the end or part nearest to the operator of the instrument and the term "distal" means the end or part farthest from the operator. The stent can be self-expandable such that it self-expands and contacts or rests on the body tissue or wall in the body cavity when the sheath is moved longitudinally away from the distal end of the core, thus releasing the radial constraining by the sheath on the stent.

The stent of the present invention has many superior characteristics which render it highly useful as scaffolding support to maintain patency of body cavities and passageways. Because the stent of the present invention can be made from a single continuous wire, compared to prior art stents, the manufacturing process of the stent of the present invention is greatly simplified and the amount of waste material resulting from manufacturing is greatly reduced, thereby reducing the cost of production.

Furthermore, the stent of the present invention overcomes many of the shortcomings of the prior art stents. For example, the zig-zag stents have many ends of wire (or wire ends), which are welded to other wire ends. With a large number of wire ends, as is present in a multiple-wired stent, special effort may be needed to shield these wire-ends or prevent them from protruding into tissue of the body. Such effort is labor-intensive. Likewise, the wire-mesh stents also have multiple wires and thus impose similar risk associated with multiple wire ends. In the present invention, using one continuous wire to make a stent reduces the number of wire ends, thus greatly lowering the risk of causing irritation or injury to body tissue. Such a single-wired stent has only two wire ends, which can easily be shielded or curved radially inward to avoid irritating or injuring body tissue.

With multiple-wired stents such as the zig-zag type stent or the wire-mesh stent, because of the interlocking or intermeshing of the wires, the stents are not very compressible and flexible. The wire-mesh stent tends to become compressed (or narrow) radially at the bend when it is flexed and lengthens longitudinally when compressed radially. In contrast, the stent of the present invention is advantageous in that it can be flexed without causing significant radial compression. Moreover, it can be compressed radially without longitudinal dimensional change. Further, using a single piece of material (such as a continuous wire) to make a stent affords the advantage that a stent of any desirable length can be made without having to join sections of wire together.

Often, balloon inflation is needed to expand prior art coil stents or wire-mesh stents fully to the desired diameter. The present invention can be self-expanding such that no external force, such as that provided by an inflating balloon, is needed to fully expand the diameter of the stent. Such self-expanding nature of the stent of the present invention obviates cumbersome and possibly trauma-causing procedures such as balloon inflation.

Furthermore, unlike the coil or helical stents that do not have means for constraining longitudinal extension and tend to stretch under longitudinally directed forces (such as the force caused by flowing fluid or movement of the vessel contacting the stent), the stent of the present invention has constraint means so that the stent does not extend longitudinally from the expanded form.

Because the deployment of thermoelastic shape-memory stents generally require ice-cold saline to maintain the stent in the soft or shrunken form or saline of relative hot temperature to expand the stent, the use of self-expanding stents obviates such cumbersome procedures. Although the stent of the present invention can be made of thermoelastic shape-memory material to render it soft and shrunken at a temperature lower than normal human body temperature (about 37° C.), the stent can also be made with other flexible material which are effective in rendering a stent capable of returning (or self-expanding) to a preprogrammed shape upon release from a deformed shape. An example of such a material is stainless steel, superelastic nitinol, or superelastic plastics. The stent can be made to have any desirable length with any number of loops or windings from a single wire without the use of external adhesion means such as welds or adhesives.

Prior art cylindrical, spikeless mandrels, such as those used for making coil-shaped stents that are expanded with balloons, are not readily adapted for making a self-expanding coil with curves from a single wire because there is no structure on such mandrels for securing the stent. The mandrel of the present invention overcomes this problem by having spikes upon which the wire can be wound. Further, the mandrel of the present invention can be used to make stents that have completely enclosed loops and still enables the removal of the stent, once formed, from the mandrel without distortion. The mandrel of the present invention can be disassemblable such that it can be taken apart without distorting a stent that has been formed thereon. This overcomes the problem that a stent tautly wound on a mandrel with spikes cannot be easily released from the mandrel. The disassemblable mandrel of the present invention greatly facilitates the forming of stents with intricate patterns of waves from single lengths of wire.

BRIEF DESCRIPTION OF THE DRAWING

These and other features, aspects and advantages of the present invention are illustrated with reference to the accompanying drawing, wherein like numerals represent corresponding parts in the several views.

DETAILED DESCRIPTION OF THE INVENTION

For purposes of illustration, the preferred embodiment of this invention is shown and described in reference to applications in angioplasty. However, applications other than in angioplasty, such as in body cavities and passageways, are practicable and no limitation in scope of the invention is intended by the embodiments.

Figures 1, 4:
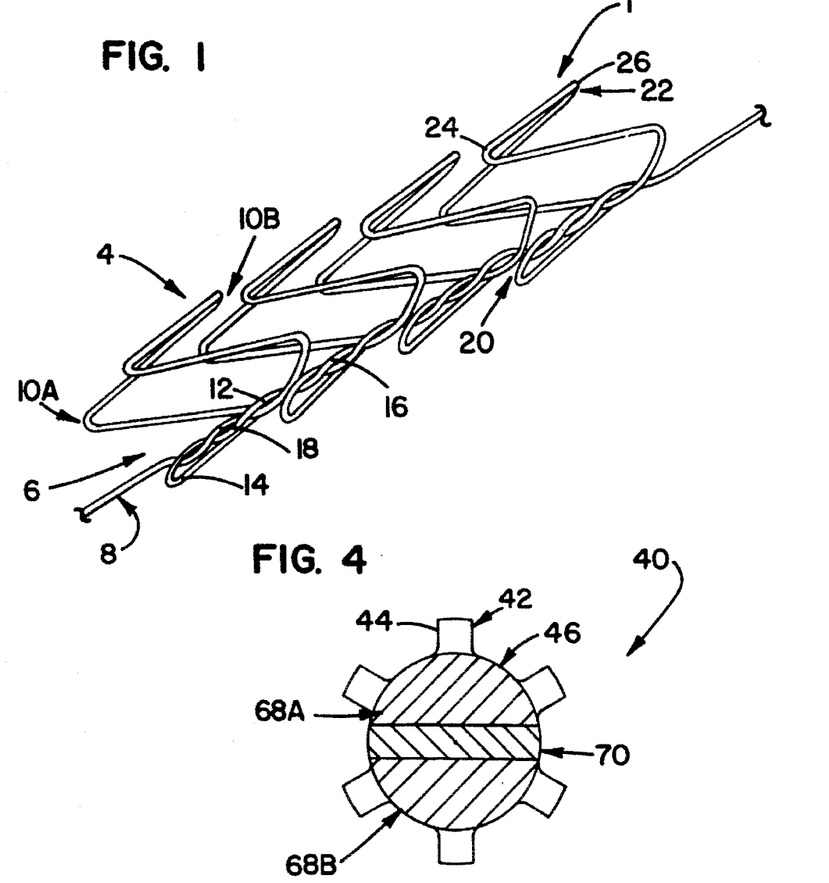
FIG. 1 is an isometric view of an embodiment of the stent in its expanded form.
FIG. 4 is an end view of a mandrel for making the stent of FIG. 1.
Figures 2, 5:
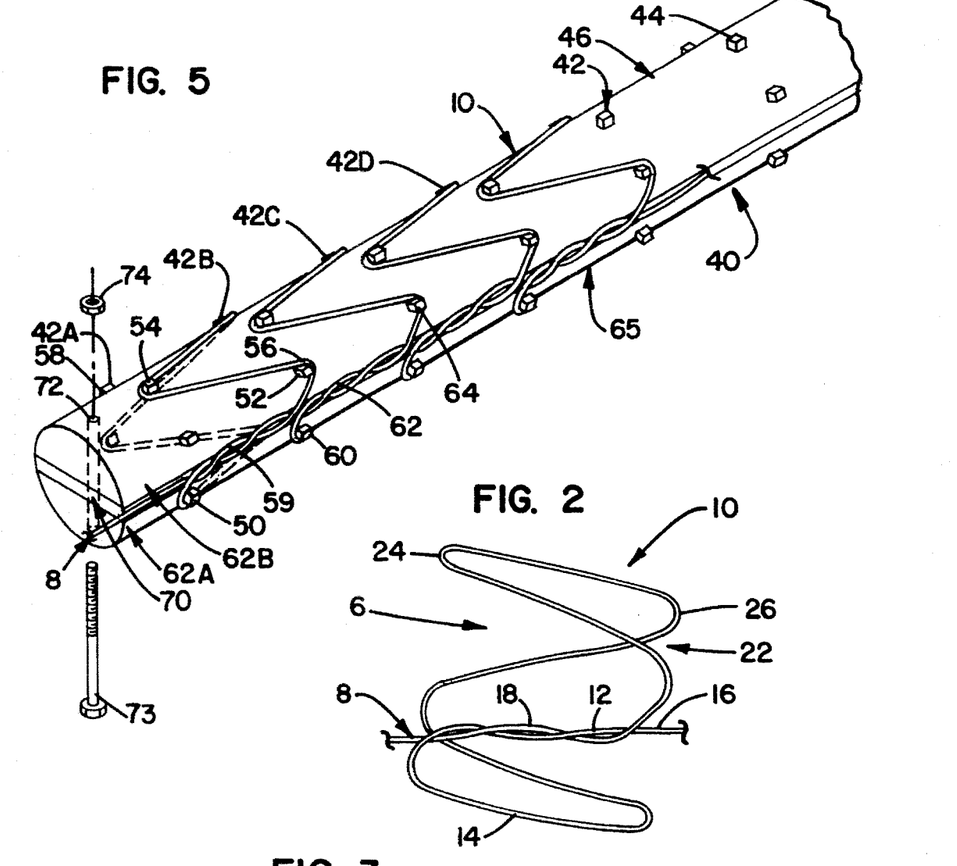
FIG. 2 is a side view of an isolated loop (or winding) of the stent of FIG. 1.
FIG. 5 is an isometric view of a portion of the mandrel of FIG. 4 with a wire mounted thereon for making a stent.
Figure 3:
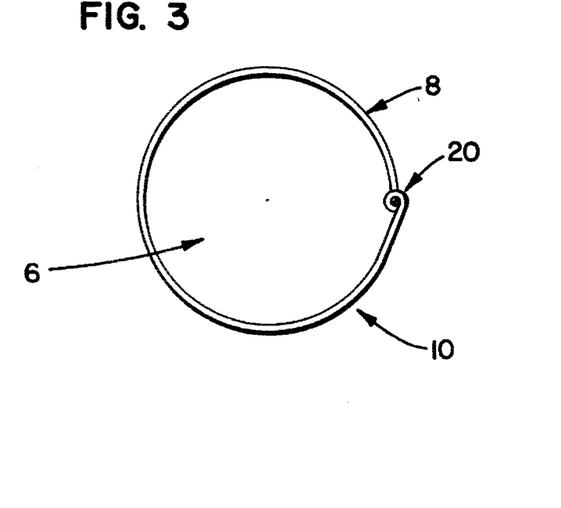
FIG. 3 is an end view of the stent of FIG. 1.

FIGS. 1–3 show the construction of an embodiment of the stent of the present invention. The stent 1 is a coil 4 having a generally cylindrical shape with an open lumen 6. That is, as shown in FIG. 3, the stent 1 has a circular cross section with an open central portion or lumen 6. A continuous wire 8 can be used to form the coil 4 such that the coil has successive windings (or loops) 10 and is prevented from stretching in its longitudinal axis. Any two adjacent successive windings 10 (or first 10A and second 10B windings) are connected and restrained from stretching longitudinally by an interconnecting portion or strip 12 of the wire. Such an interconnecting portion of wire 12 is integrally connected to a first end portion 14 of the first winding 10A and an end portion 16 of the second winding 10B and intertwined with a second end portion 18 of the first winding 10A. Thus each winding (e.g. 10A) forms a loop closed by intertwining, wherein one end portion (e.g. 14) of the winding is integrally connected to the interconnecting portion (e.g. 12) of the wire and the other end portion (e.g. 18) of the winding (e.g. 10A) is intertwiningly connected to the same interconnecting portion (e.g. 12). Such intertwining of the interconnecting portions of the wire along the length of the stent results in an aligned, generally straight, longitudinal spine (or cord) 20 in the stent 1. The intertwining of the interconnecting portion of the wire with an end portion of a winding secures the windings in relation to one another to maintain the geometry of the stent and prevent stretching of the stent longitudinally or axially. The number of turns in the intertwining can vary depending on the distance between successive windings. In a stent 1 with only one spine 20, because the portions of the windings 10 on the part of the cylindrical coil opposite the spine are not rigidly held together but have freedom of movement, the stent can be flexed without significant narrowing of the lumen 6 at the bend as a result of the flexion.

Referring to FIG. 2, a winding (or loop) 10 has curves (or waves) 22, which have peaks 24 each with a valley 26 adjacent and associated therewith. As referred to herein, peaks generally are oriented in the same direction. Preferably, the curves 22 in a winding 10 are generally sinusoidal in appearance and each has one peak 24 and one valley 26. In a sinusoidal wave, a wave of one wavelength exists between two adjacent points having the same phase. The peaks and valleys can have smooth turns resembling a ture sine wave rather than sharp turns as in a zig-zag form. This is particularly true in the case where a stiff material such as a nitinol wire is used to form the stint. In the formation process of the stent, the stiffness of the wire facilitates the smooth curving of a winding as the wire is bent. Depending on the size of the body cavity to be supported by the stent, the size of the curves and number of curves 22 or peaks 24 in a stent 1 can vary. For example, a stent 1 having an expanded outside diameter of about 3 mm can have two peaks 24 or curves 22 whereas a stent designed to have an expanded outside diameter of 1 cm can have four or more (for example, eight) peaks. The distance between adjacent loops or windings 1 can also vary depending on the supporting strength desired and the size of the body cavity to be supported by the stent. For example, a stent having an expanded diameter of about 0.7 cm can have windings that are about 0.5 cm apart from peak to peak along the longitudinal axis.

The wire 8 for making the stent can be a flexible material of adequate strength for making self-expanding stents, such as stainless steel, plastic polymeric material, shape-memory material (e.g., nitinol), and the like. The use of nitinol and shape-memory material for making stents has been disclosed in U.S. Pat. No. 5,147,370 (McNamara) and in "Shape-Memory Alloys," *Scientific American*, Vol. 281, pages 74–82, November 1979, the disclosure of which relating to the methods of making stents from such shape-memory material is incorporated by reference herein.

Preferably, the stent is made of a superelastic shape-memory material, such as one made with superelastic nitinol. The stent can also be made with thermoelastic shape-memory material, which can also be made of nitinol. Nitinol alloys as an implant material have been established to be biocompatible. A number of permanent implants made from nitinol have been used in humans. Nitinol is also resistant to corrosion, oxidation, and abrasion. Nitinol wires and structures of other shapes are commercially available, for example, from suppliers such Shape Memory Applications Co. and Flexmedics Co.

A stent made from a flexible or superelastic material can be compressed into a smaller size (i.e. smaller diameter and/or shorter length) to fit and be confined inside a catheter-like instrument for delivery of the stent to a desired location in the body cavity. When the stent is released from the instrument, the flexibility of the flexible material causes the stent to spring back to its shape and size before compression.

A stent made of a thermoelastic shape-memory material can also be made by forming the material into a desired size and shape and annealing at a temperature higher than the transition temperature to program the stent to have that desired size and shape. After cooling the stent to a temperature below the transition temperature, the stent becomes soft and can be reduced to a smaller size by crushing or compressing by force so that it can be delivered to the selected location in the body cavity while maintaining the temperature of the stent at below the transition temperature. As long as such below-transition-temperature is maintained, the stent remains at its reduced size without subjecting to an externally applied compression. When the stent is warmed to a temperature above the transition temperature, the stent returns to the preprogrammed size and shape (i.e., the size and shape before the stent was crushed).

The stent can also be coated with a substance for reducing the risk of thrombosis and preventing undesirable depositions thereon. For example, appropriate coatings, such as silicone rubbers, hydrophilic polymers, fibrin, coatings containing heparin, collagen, and the like may be used on the stent. The curves of the stent, upon expansion, rest and press on the wall of the body cavity, thereby exerting a pressure on the wall to prevent the collapse of the wall of the body cavity.

A stent of the present invention can be made by winding a single continuous wire, such as a nitinol wire, on a preformed cylindrical jig or mandrel to obtain the coil with the right configuration of curves. FIG. 4 shows the end view of an embodiment of a mandrel used for forming the coil of a stent of FIG. 1. The mandrel 40, as shown in FIG. 4, has a diameter of about 0.4 cm and rows (or rings) 42 of spikes 44 disposed longitudinally 0.5 cm apart on the outer surface of the mandrel. Each ring 42 of spikes contains six spikes 44 arranged evenly as a ring-like configuration on the outer surface 46 of the mandrel. The spikes 44 are about 0.1 cm high and about 0.7 mm×0.7 mm in cross section.

FIG. 5 shows how a wire 8 made of nitinol is wound on the mandrel around (or upon) the spikes to form a stent with the configuration of FIG. 1. The wire 8 is wound on the spikes 44 of two different rings to form a generally sinusoidal winding 10 with curves. A first end (not shown) of the wire can be anchored or secured on the mandrel 40 so that the wire 8 can be wound upon the spikes 44 tautly. The wire extends past the last spike 50 of the first ring 42A of spikes to the second ring 42B of spikes and winds upon the first spike 52 of the second ring of spikes, then extends back to wind upon a spike (the second spike 54) on the first ring 42A of spikes, thereby forming the first valley 56 and peak 58 of the first winding (the order of the rings and spikes are arbitrarily assigned for convenience of reference). The wire is then wound upon the spikes in the second and first rings of spikes alternately in a wavy fashion to form the wavy loop of the first winding. The wire wound upon the last spike 50 of the first ring 42A of spikes extends to the third ring 42C of the spikes while intertwining with the portion 59 of the wire extending from the first end of the wire between the first ring 42A of spikes and the first spike 52 of the second ring 42B of spikes. Similarly, the wire wound upon the last spike 60 of the second ring 42B extends to the fourth ring 42D of the spikes while intertwining with the portion 62 of the wire extending between the second ring 42B of spikes and the first spike 64 of the third ring 42C of spikes. This portion 61 of wire can be considered the interconnecting portion interconnecting the first winding 42A and the second winding 42B. The portion of wire 59 extending from the first ring 42A of spikes to the first spike 52 of the second ring 42B of spikes is an end portion of the first winding 10A (see FIG. 1) and the portion of wire 62 connected with the interconnecting portion 61 and extending to the first spike 64 of the third ring 42C of spikes is an end portion of the second winding 10B. The process for forming a winding can be repeated to wind the wire alternately upon the spikes of the second and third rings of spikes to form the second winding. Depending on the length of the wire in the interconnecting portion, the number of intertwining twists (or turns) therein can vary, typically from about 0.5 to about 4.5, preferably 1.5 intertwining twists between adjacent windings. An intertwining twist (or turns) herein refers to a 360° turn of the double helix formed by the intertwining of two wires. This process for forming successive windings can be continued until a stent of desired length is formed on the mandrel.

After the wire is wound on the mandrel, the other end (not shown) can be secured to the mandrel as does the first end. The wire ends can be secured to the mandrel by methods such as tying a knot on a structure such as a spike or being gripped by a clamp. The wire ends can be secured in such a way that they are turned radially inward on the mandrel so that when the finished stent is deployed the wire ends will not protrude into the body tissue. This can be done, for example, by providing a depression on the surface of the mandrel on which the wire end is clamped.

Subsequently, the mandrel with the wire mounted thereon can be annealed at about 500° C. for about 30 minutes and then cooled to room temperature. Methods of annealing nitinol material is widely known in the art and can be used for preprogramming the stent of the present invention to attain a desired configuration or shape. The stent can then be removed from the mandrel.

The mandrel can be made with a material that can maintain mechanical integrity for the wire to be wound thereon and undergo temperature changes for annealing. An example of material effective for construction of the mandrel is a metal such as aluminum, titanium, or nickel; or an alloy such as carbon steel, stainless steel, or MONEL. As previously stated, the mandrel of the present invention is preferably disassemblable to facilitate the removal of a formed, wound stent therefrom. The mandrel can have spikes or projections disposed on the outer surface thereof upon which the wire can be wound to form the stent. The spikes can be cylindrical, has a square cross section, or other similar shapes as long as a wire can be firmed wound upon them. Other than spikes, means on which the wire can be wound, such as hooks, or slits cut on the mandrel, can be used to form the curves of the stent.

Preferably, the mandrel can be disassembled so that the stent can be released therefrom without being distorted either radially or longitudinally. As used herein, a stent is "distorted" if after removal from the mandrel, external force is needed to shape the stent back to the form prior to removal. Referring to FIGS. 4–5, which shows the detail structures of an embodiment of the mandrel of the present invention, the mandrel 40 has spikes 44 and a cylindrical body 65 which includes three layers. The two external (or end) layers 68A,68B of the cylindrical body each has a lateral (or transverse) cross section that is shaped generally like a segment of a circle defined by an arc and a chord. All of the spikes 44 are disposed on such external layers 68A,68B. The third layer 70 of the cylindrical body is an intermediate layer disposed between and separating the external layers 68A,68B. Such intermediate layer 70 is a strip or a spacer having a lateral (or transverse) cross section that is generally rectangular. Each of the three layers can have holes 72 proximate its ends through which screws 73 can extend. The three layers of the mandrel can thus be secured together at the two ends with screws 73 and bolts 74.

Figure 6:
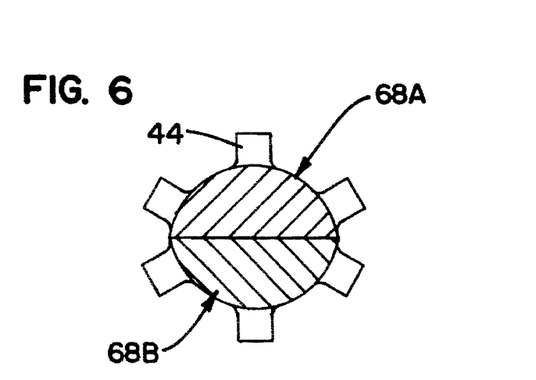
FIG. 6 is an end view of the structure resulting after a mandrel of FIG. 5 has been partially disassembled and parts removed therefrom.

To remove a formed (or wound) stent from the mandrel shown in FIGS. 4–5, the bolts 74 and screws 73 are removed from the ends of the mandrel 40 so that the three layers of the mandrel are no longer secured together. The intermediate layer 70 can then be withdrawn (or removed) from the mandrel 40, enabling the two external layers 68A,68B to be brought together. Now referring to FIG. 6 (FIGS. 5–6 are not drawn to scale, the spikes are shown larger proportionally compared to the overall size to show structure), the two external layers 68A,68B, after being brought together, results in a structure that is still generally cylindrical but has a smaller transverse, cross-sectional area than that of the three-layered mandrel. The thickness of the intermediate layer 70 is selected such that the transverse cross section of such two-layered structure has a perimeter that is small enough to enable the windings of the stent to be lifted off the spikes, thus releasing the stent from the mandrel. At least one layer (68A or 68B) of the two-layered structure can then be slid out of the stent at a time. In this way, the stent can be removed from the mandrel without distortion.

In another embodiment, the mandrel can have spikes that are movably affixed thereon. For example, the spikes can be made of screws that can be removably screwed into the cylindrical body of the mandrel. To separate a formed stent from the mandrel without distortion, the screws can first be removed by unscrewing from the cylindrical body.

Figure 7:
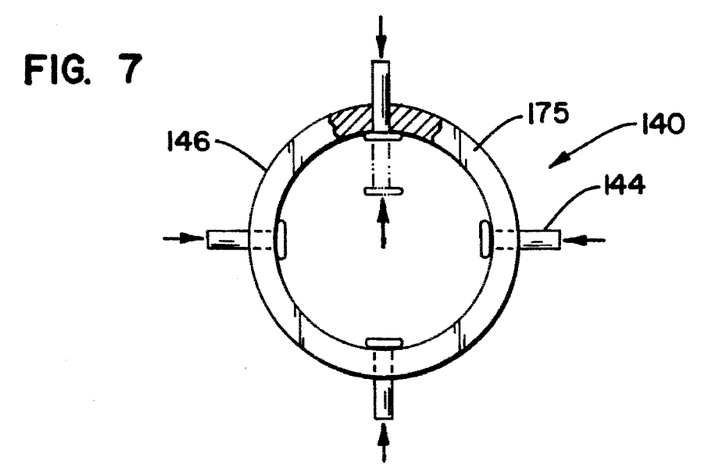
FIG. 7 is a plan view viewing from the end of another embodiment of a mandrel of the present invention wherein spikes have been pushed below the cylindrical surface of the mandrel.

In yet another embodiment, as shown in FIG. 7, the spikes can be slidably affixed in holes on the cylindrical body. The spikes 144 can extend out of the cylindrical outer surface 146 of the cylindrical body (of the mandrel) for the wire to be wound thereupon. When the stent has been formed, the spikes 144 can be forced (for example, by pushing with a finger) proximate or below the outer cylindrical surface 146 of the mandrel 140. This results in a mandrel 140 wherein the spikes 144 do not extend out of the surface 146 of the cylindrical body. The stent can then be slid off the mandrel. The mandrel can have a annular outer shell 175 through the spikes extend. A means, such as a core (not shown) that fits inside the shell 175, can be used to push the spikes 144 out of the outer cylindrical surface 146 of the mandrel 140 for a wire to be wound thereon. Such a mandrel is particularly well adapted to be used in mass-producing the stent. For example, to further facilitate removal of a formed stent, a means can be used to extend the spikes as a group in and out of the cylindrical surface 146 of the mandrel such that the spikes do not have to be pushed individually.

A stent formed with a superelastic material by the method described hereinabove can be deformed, compressed or flexed to various shapes and will immediately return to its preprogrammed, annealed shape on release of the externally applied force. Since the stent can be formed to have any desired length, it can be formed to have the exact length needed for a particular application. Alternatively, a stent of a desired length can be formed by trimming the ends off a longer stent. A long stent can also be divided into shorter stents.

Figure 8:
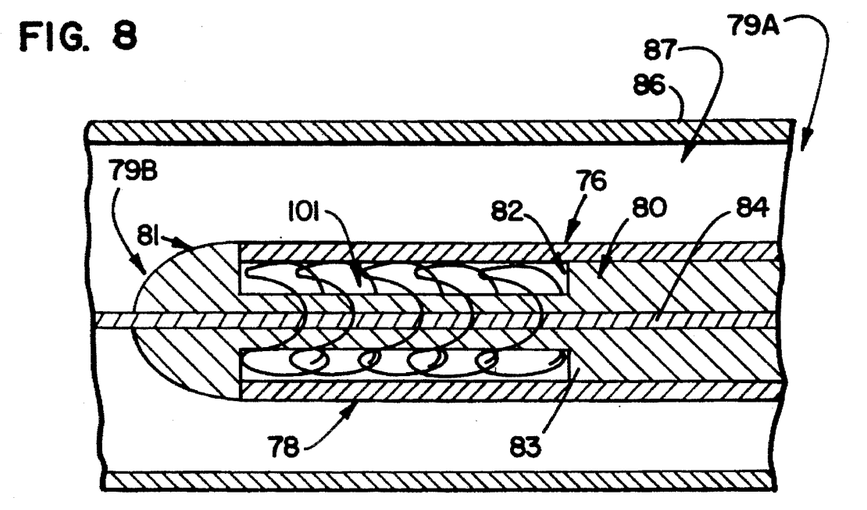
FIG. 8 is a side elevation in section of an instrument for deploying a stent of the present invention with the stent mounted therein in a blood vessel.
Figure 9:
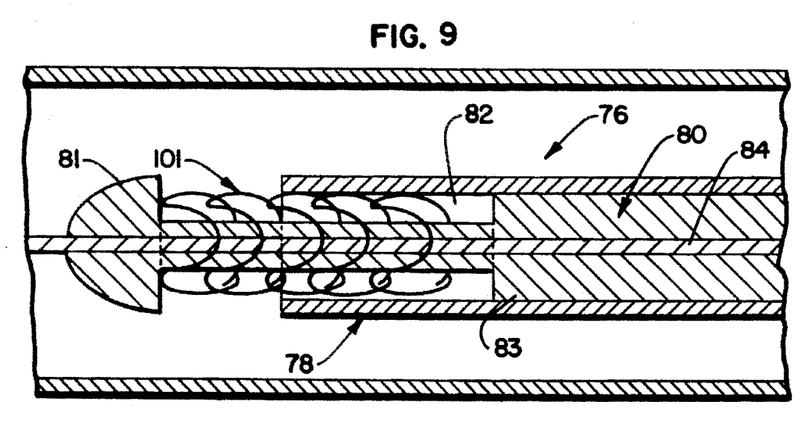
FIG. 9 is a side elevation of the instrument of FIG. 8 showing a partly deployed stent in a blood vessel.

The self-expanding stent of the present invention can be used to provide scaffolding support to hollow organs or passageways or channels which are narrowed. The stent can also act as a skeleton to fashion vascular grafts for the treatment of aneurysms of vascular structures. The stent is preferably delivered to, placed or deployed in a desired or selected location by using a catheter-like instrument. FIG. 8 and FIG. 9 show such an embodiment. The instrument has an elongated tubular outer sheath (or sleeve) 78 having a first or proximal end 79A and a second or distal end 79B. The sheath can be a conventional catheter. The instrument also includes an elongated core or pusher device 80 having a first or proximal end and a second or distal end movably or slidably disposed within the sheath. The core 80 can have a generally blunt, conical or hemispherical tip, nose, or terminal piece 81 proximate or at its distal end. The sheath and core can be made with conventional material effective for making catheters. The conical tip 81 of the core 80, being on the distal end 79B of the instrument, facilitates the introduction of the instrument through a narrow body channel into the desired location of the body cavity. The conical tip 81 has a diameter at the base of the cone approximately equal to the outside diameter of the sheath 78. The core 80 also has an annular recess 82 defined by the conical tip 81 and a plug 83 some distance away from the conical tip toward the proximal end of the core. The core 80 can be drawn such that the conical tip is proximate to the distal end of the sheath 78 so as to confine a stent within the sheath. A stent 101 of the present invention loaded (or seated) in the recess 82 of the core 80 is compressed and secured (or restrained) from expanding radially by the sheath 78. Because the stent of the present invention is highly compressible, it can be confined in the recess of the core by the sheath and the core.

Figure 10:
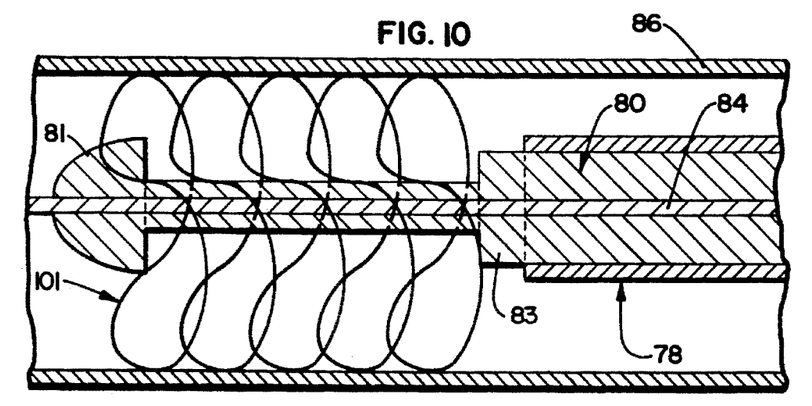
FIG. 10 is a side elevation of the instrument of FIG. 9 showing a fully deployed stent in a blood vessel.

The instrument can have a channel running through the center of the core longitudinally. A guide-wire 84 can be provided to extend from one end of the core 80 through the channel and out the other end of the core 80. The catheter-like sheath 78 with a stent restrained therein is positioned across the area to be stented by passing over the guide-wire 84. Methods of positioning catheters, such as one with the aid of a guide-wire, are widely known in the art. Such standard methods can be utilized to position the instrument with the loaded stent in a desired location. After the instrument has been positioned in a desired location, the sheath 78 is gently drawn or pulled back while the core 80 is maintained stationary. As the sheath 78 is pulled backwards in the proximal direction, the now unconstrained stent 101 springs open or expands radially due to its flexibility or memory for its predetermined or preprogrammed state, as shown in FIG. 10. The windings of the stent rest and press on the wall 86 of the body cavity 87. The sheath 78, the core 80, and guide-wire 84 are then withdrawn from the body cavity 87. Once expanded, the open cylindrical lumen of the stent has a diameter larger than both the conical tip 81 and the sheath 78, therefore the instrument 76 can easily be withdrawn without snagging or catching the stent 101.

Figure 11:
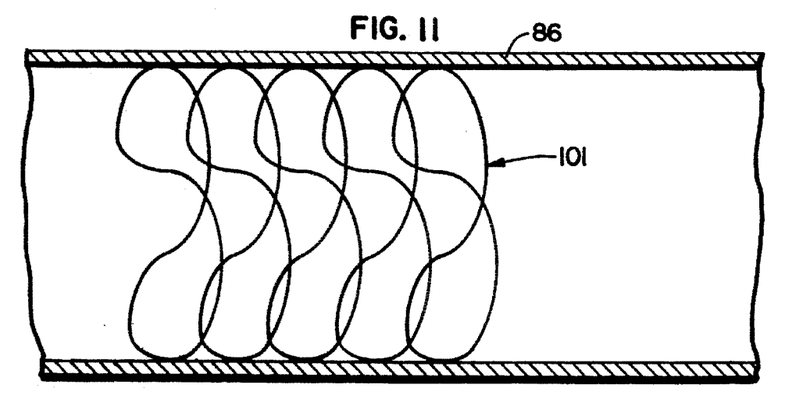
FIG. 11 is a side elevation showing a stent of the present invention deployed in a blood vessel.

Due to the wavy shape of the windings, the stent provides scaffolding support to maintain patency of the body cavity without the body tissue collapsing or protruding into the cylindrical lumen of the stent around the wires, as shown in FIG. 11. The spine (not shown in FIGS. 8–11 for reason of simplicity) prevents the stent 101 from stretching during the deployment of the stent as well as over time as the stent rests in the body cavity after deployment. The high longitudinal flexibility of the stent reduces trauma to the body tissue.

In a further embodiment of the invention, the stent can be made of a thermoelastic shape-memory material that can be rendered soft and shrunken at a temperature below normal body temperature, for example, a material that has a transition temperature of about 30°–60° C. A stent made of such a material can be deployed in the body cavity by an instrument and method as disclosed in U.S. Pat. No. 5,037,427 (Harada et al.), which description relating to the instrument and method of deployment of the stent is incorporated by reference herein.

Figures 12, 13, 14:
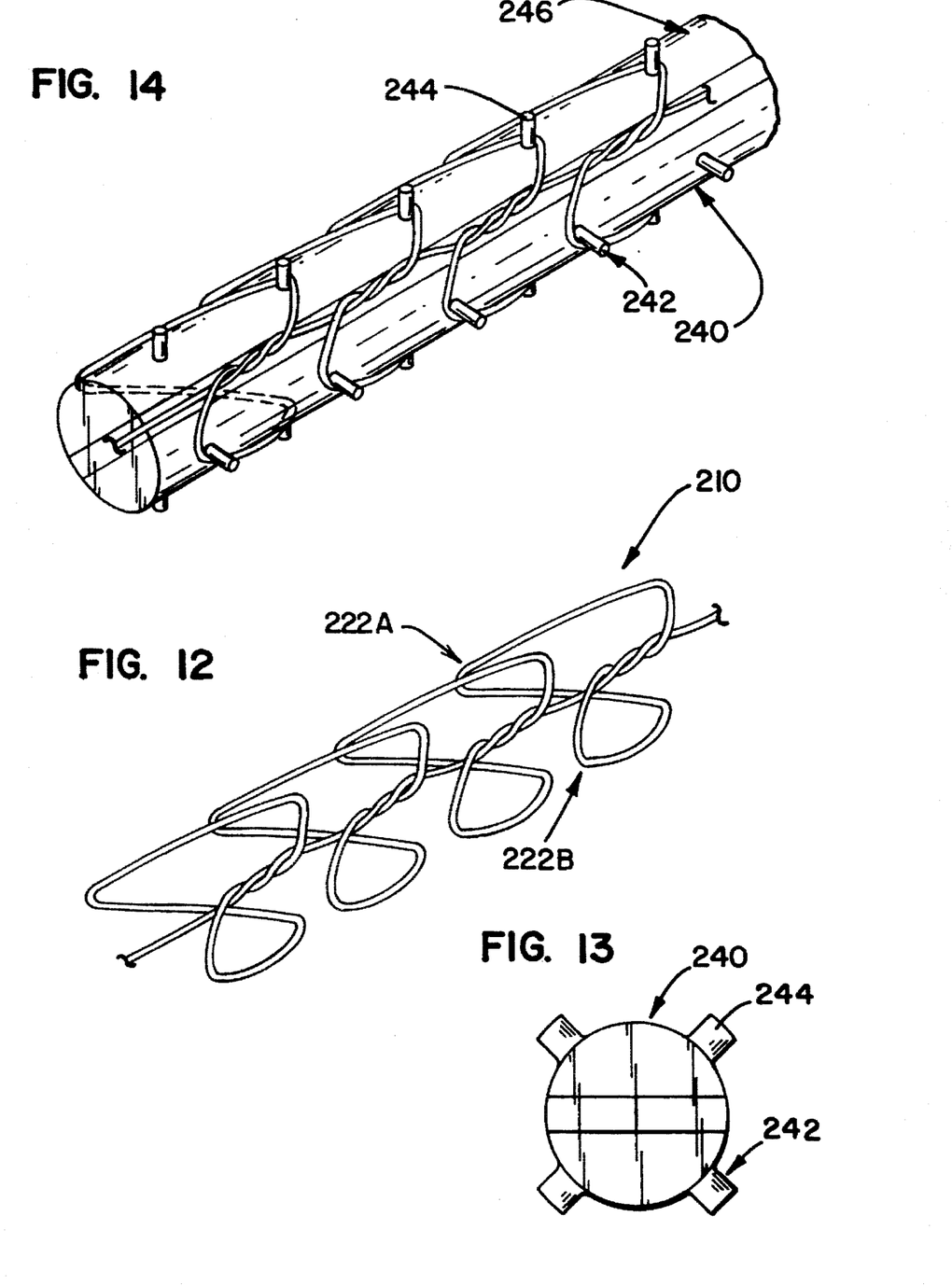
FIG. 12 is an isometric view of another embodiment of the stent according to the invention.
FIG. 13 is an end view of the mandrel for forming a stent shown in FIG. 12.
FIG. 14 is an isometric view in section of a mandrel with a stent of FIG. 13 wound thereon.

The number of windings, the longitudinal distance between windings in the stent, and the number of curves in a winding can vary depending on factors such as the dimensions of the body cavity in which the stent is to be positioned, the physiological condition of the tissue in the body cavity, the material selected for making the stent, and the wire thickness : interloop gap ratio selected. FIG. 12 is another embodiment of the stent of the present invention. This stent 201 has two curves or waves 222A,222B oriented in the same direction in a single winding 210. Such a stent is made by winding on a mandrel 240 having an end view as shown in FIG. 13 and an isometric view of a portion thereof as shown in FIG. 14. The mandrel 240 has rings 242 of spikes 244 disposed on the outer surface 246 thereof. Each ring 242 of spikes 244 contains four spikes evenly spaced around the circumference of a circle corresponding to the cross section of the mandrel 240. As can be seen in FIG. 13 and FIG. 14, the corresponding spikes 244 in different rings 242 are aligned (or arranged) in longitudinal straight lines (or columns) such that viewing from the end of the mandrel, only the four spikes proximal to a viewer are visible. However, the spikes in different rings can also be arranged in a regular but nonstraight fashion instead of in straight columns, for example, as in twisted, parallel lines.

EXAMPLES

Stents were made according to the procedure described hereinabove each using a single continuous piece of superelastic nitinol wire and a mandrel shown in FIG. 4 and FIG. 6 such that each wire was fashioned into a cylindrical stent about 3 cm long and 0.4 cm in diameter in the fully expanded state. A superelastic nitinol wire 8 of 0.1 mm diameter was wound on a generally cylindrical mandrel 40 of about 0.4 cm diameter with rings 42 of spikes 44 disposed about 0.5 cm longitudinally apart on the mandrel. Each ring 42 of spikes contained 6 spikes 44 evenly spaced apart on the circumference (or perimeter) of the ring. Each spike 44 was 1 mm high and had a transverse cross section of 0.7 mm×0.7 mm. After a stent 1 was formed on the mandrel and annealed at 500° C. for 30 minutes, it was placed, compressed and confined (or secured) in the recess space 82 of a catheter-like instrument 76 described hereinabove for placement or deployment into a coronary artery of a dog. Seven dogs, weighing between 22 Kg and 30 Kg, were used in the study. The stents were deployed in the coronary arteries of the dogs by utilizing a 5 French delivery instrument or catheter (i.e., the sheath has an outside diameter of 1.67 mm) as illustrated in FIGS. 8–10. Of the seven dogs, one died during the procedure of placing the stent, six were successfully stented, each with a stent deployed in the coronary artery. The dogs were sacrificed after two to eight months to investigate the patency of the coronary arteries where the stents were deployed. All of the stented arteries were found to be patent with minimal intimal hyperplasia (or narrowing). The canine studies were performed according to a protocol approved by the Animal Care Committee (Protocol No. 9011022) of the University of Minnesota.

Figure 15:
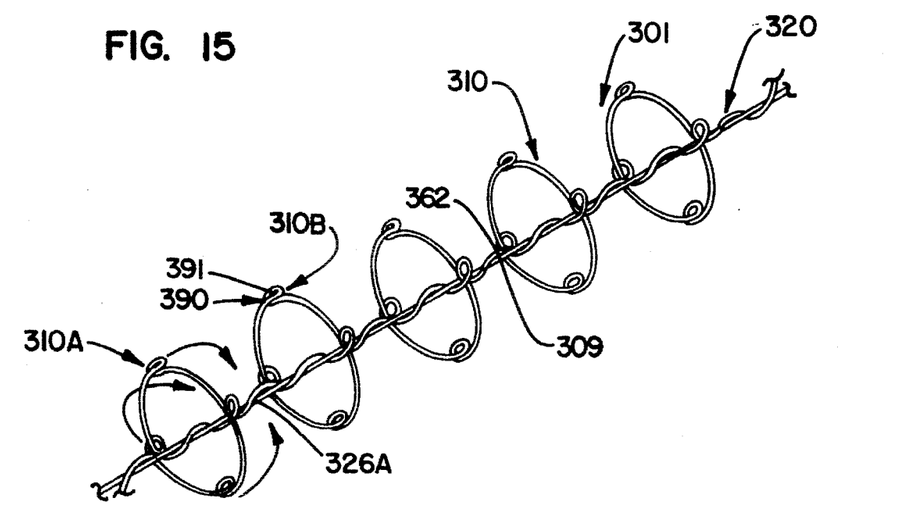
FIG. 15 is an isometric view of another embodiment of the stent according to the invention.
Figure 16:
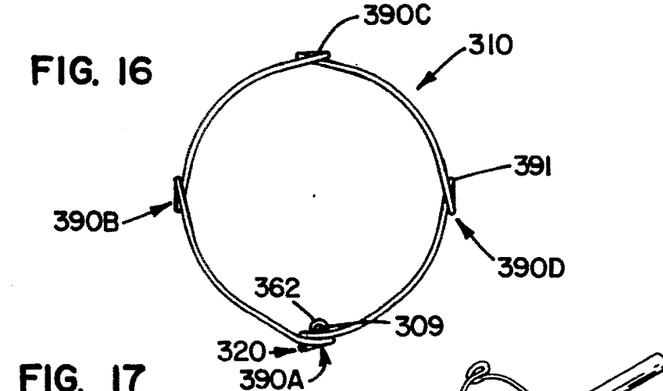
FIG. 16 is an end view of the stent of FIG. 15.

Referring to FIG. 15, a stent 301 of another embodiment has individual windings (or loops) 310 wherein adjacent loops are interconnected by a strip (or portion) 362 of wire, which intertwines with a portion of wire 309 that runs along the length of the stent to maintain the geometry of the stent and prevents the longitudinal stretching of the stent. A spine is formed by the intertwining of interconnecting portions of wire with the lengthwise-running portion of wire. One or more of the windings (or loops) 310 in the stent can have one or more eyelets 390 fashioned in it. The eyelets are little loops formed on the perimeter of the individual windings which are interconnected by the spine 320. As shown in FIG. 16, each winding 310 is generally circular in outline. An eyelet 390 is formed as a tight turn of the wire, forming a small loop on a spike when the stent is wound on a mandrel (not shown). Four eyelets 390 can be formed on a winding 310, one on the spine 320 and three spaced from the spine.

Such a stent can be form by running a generally straight wire 309 along the length of the mandrel (not shown) and then bending the wire back to run in the opposite direction at the end of the mandrel before forming the first winding 310A. After a winding (e.g. 310A) is formed, the portion of wire (e.g. 362A) interconnecting the previously formed winding (e.g. 310A) and the next winding (e.g. 310B) is intertwined with the generally straight portion 309 (i.e., the portion that runs lengthwise on the mandrel) of the wire. Then the next winding (e.g. 310B) is formed.

The eyelets can function as torsion springs and permit the winding to be collapsed by flexion at the eyelets when the loop or winding is compressed radially. For example, when a winding 310 is compressed by applying force on the eyelet 390A on the spine 320 and the eyelet 390C opposite the spine, the winding will collapse (or flex) about the other eyelets 390B, 390D. In other words, the generally circular winding will be transformed into two semicircular segments that are hinged to flex in a book-like fashion about the eyelets 390B, 390D adjacent to but spaced from the spine 320. Likewise, when the eyelets adjacent to but spaced from the spine 320 are compressed, the winding collapses about the spine and about the eyelet 390C opposite the spine. By compressing the winding to flex about all the eyelets simultaneously, the winding can be collapsed to a geometry (or size) to fit inside a deployment instrument (such as the one shown in FIG. 8) that constrains the radial dimensions of the stent. A stent, having its windings thus collapsed, can be deployed in a selected site in the body. Upon deployment, the stent can spring back to its unconstrained dimension (i.e. preprogrammed shape) to maintain the patency of the body cavity or passageway. The eyelets, other than functioning as torsion springs, also help to provide more contact surface area for scaffold-supporting the wall of the body cavity. Such an embodiment would be preferred for large stents with diameters of 10 mm to 30 mm.

Various modification can be made on the above embodiments. For example, the loop on an eyelet can be wound on a spike clockwisely or counterclockwisely and the number of eyelets on a winding can vary. The eyelet on the spine can be eliminated by, at the beginning and end of a winding, turning the wire 90° at the spike aligned with the spine instead of forming a loop-shape eyelet thereon. Such a stent can still be collapsed by radial compression. The elimination of this eyelet may also enhance the longitudinal integrity against stretching. On the other hand, more eyelets can also be made on a winding to provide more points upon which the winding can flex. In addition, in closing a winding on the mandrel, a knot can be tied after the winding has been wound on the mandrel, securing the two ends of the winding together on the spine. The knot can be but is preferably not tied onto a spike so that the wire on which the knot is tied can be gripped more tightly by the knot to further prevent the longitudinal stretching of the stent. Such a stent with knots for closing windings can even be made without the generally straight wire running along the length of the stent for intertwining with the interconnecting portions.

Figure 17:
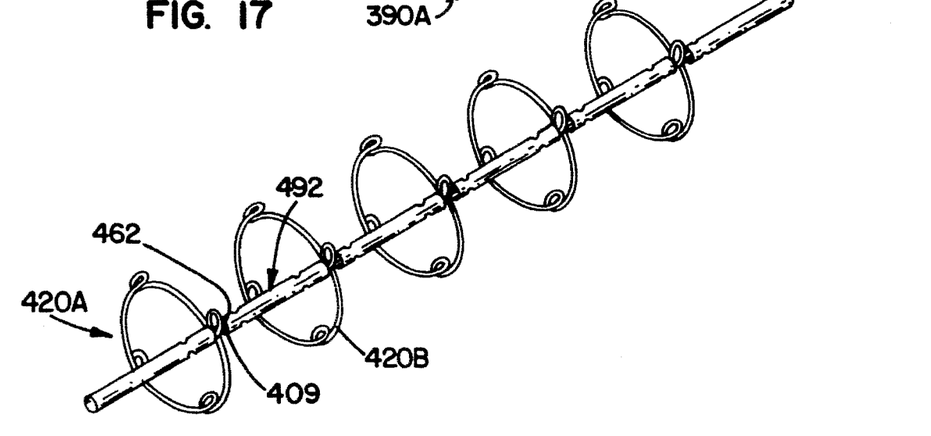
FIG. 17 is an isometric view of yet another embodiment of the stent according to the invention.

The above embodiment can further be modified, as shown in FIG. 17 by using crimpable (or pinchable) sections 492 of tubing to encircle and hold the interconnecting portions 462 of the wire onto the generally straight portion 409 of the wire. After a winding (e.g. 420A) is formed, the free ends of the wire (i.e., the free end of the generally straight portion 409 of the wire and the free end of the wire extending from the newly formed winding which will become an interconnecting portion 462 of the wire) are threaded through a section of a crimpable tubing 492 made of a deformable material without shape-memory (e.g., stainless steel, titanium). These free end portions of the wire are then threaded through the section 492 of tubing until the section of tubing is proximate to the newly formed winding (e.g. 420A). Then a tool, such as a pair of crimping pliers (not shown), is used to crimp or pinch the section of tubing 492 onto the portions of wire so that they are held fast by the crimped section of tubing. Likewise, before a winding (for example, the first winding formed on a stent) is formed, the portions of the wire can be held fast in a similar manner. The stents of the above embodiments can be made with superelastic nitinol with the annealing method and disassemblable mandrel described hereinabove.

In yet another embodiment, the stent can be made, rather than from a single wire, by fashioning out of larger pieces of material, such as punching the desired stent configuration out of a single integral piece of material (e.g. a nitinol tube), cutting the desired stent configuration out of metallic structures using dies, or chemically etching out of a tubular structure. Methods of punching, die-cutting, chemical etching, and the like, are known in the art and can be used for making such stents. Stents can be fashioned with such methods to have a structure substantially similar to the single-wired stent described hereinabove. Such a stent can have a cylindrical body which includes a plurality of wavy closed windings (or loops) and strips interconnecting the windings such that the stent is prevented from stretching longitudinally. The strips can be interconnected to form an aligned longitudinally oriented spine. Such a stent can be made of the material described hereinabove and can be self-expandable from a first radially-constrained, unexpanded diameter to a second, radially-unconstrained, expanded diameter.

The methods for making the stent of the present invention can also be automated to mass-produce the stent.

It is to be understood that even though numerous characteristics and advantages of the present invention have been set forth in the foregoing description, together with details of the structure and function of the invention, the disclosure is illustrative only, and changes may be made in detail, especially in manners of shape, size and arrangement of parts without departing from the spirit and scope of the invention.

What is claimed is:

1. A stent comprising, a self-expandable cylindrical body made from a single piece of material, the stent having a longitudinal dimension, said cylindrical body including a plurality of closed windings and strips intermediate the closed windings such that said stent is prevented from expanding generally in the direction of said longitudinal dimension, said self-expandable cylindrical body exhibiting at least a spring-like behavioral component in a radial direction upon self-expanding from a first radially-constrained unexpanded geometry, to a second radially-unconstrained expanded geometry.

2. The stent of claim 1 wherein the strips are aligned to form a longitudinally oriented spine.

3. The stent of claim 1 wherein at least one closed winding is wavy.

4. The stent of claim 1 wherein the cylindrical body is formed from a single piece of wire.

5. The stent of claim 4 wherein at least one closed winding has at least a plurality of eyelets about which the closed winding can be flexed for imparting said spring-like behavioral component to the cylindrical body of the stent, upon self-expansion from the first radially-constrained unexpanded geometry, to the second radially-unconstrained expanded geometry.

6. The stent of claim 4 wherein a portion of the wire extends generally in the direction of the longitudinal dimension of the stent and intertwines with portions of the wire that interconnect adjacent windings.

7. The stent of claim 4 wherein a generally straight portion of the wire extends throughout the length of the stent and said stent further comprising a tubing section encircling a portion of the wire integrally interconnecting adjacent windings and a portion of the straight portion of wire, wherein the tubing section is crimped to secure the portions of wire encircled therein to prevent the longitudinal stretching of the stent.

8. The stent of claim 5, wherein said at least one closed winding includes a torsional spring.

9. A system for positioning in a body cavity a self-expandable stent, comprising:

an instrument for deployment of a self-expanding stent by releasably holding therein the stent in a first radially-constrained unexpanded geometry; and a self-expanding stent releasably held by said instrument, said stent comprising, a self-expandable cylindrical body formed by a continuous wire, the stent having a longitudinal dimension, said cylindrical body including a plurality of closed windings and strips intermediate the closed windings such that said stent is prevented from expanding generally in the direction of said longitudinal dimension, said self-expandable cylindrical body exhibiting at least a spring-like behavioral component in a radial direction upon self-expanding from the first radially-constrained unexpanded geometry, to a second radially-unconstrained expanded geometry.

10. The system of claim 9 wherein the instrument comprises an elongated tubular outer sheath having a first end and a second end for radially constraining said stent, an elongated core having a first end and a second end movably disposed within said sheath, the first end and second end of the sheath correspond to the first end and second end of the core respectively, said core having means for constraining the stent from moving longitudinally relative to said core, said core being longer than the sheath, said stent being releasably held within a space defined between said sheath and said core, wherein said stent self-expands and is deployed in the body cavity upon moving the sheath longitudinally away from the first end of the core, thereby releasing the radial constraint by the sheath.

* * * * *